(12) United States Patent  
Terrill et al.

(10) Patent No.: US 8,246,664 B2
(45) Date of Patent: Aug. 21, 2012

(54) MULTIPLE BONE FUSION PLATE

(75) Inventors: Lance Nathan Terrill, Dallas, TX (US); Brandon G. Beckendorf, Arlington, TX (US)

(73) Assignee: OsteoMed LLC, Addison, TX (US)

( * ) Notice: Subject to any disclaimer, the term of this patent is extended or adjusted under 35 U.S.C. 154(b) by 681 days.

(21) Appl. No.: 12/391,653

(22) Filed: Feb. 24, 2009

(65) Prior Publication Data

US 2010/0217328 A1  Aug. 26, 2010

(51) Int. Cl.
*A61B 17/80* (2006.01)
(52) U.S. Cl. .................. 606/286; 606/280; 606/283
(58) Field of Classification Search .......... 606/70–71, 606/281–286, 289, 291, 298–299, 280
See application file for complete search history.

(56) References Cited

U.S. PATENT DOCUMENTS

| 1,025,008 A | 4/1912 | Miner |
| 1,105,105 A | 7/1914 | Sherman |
| 1,869,726 A | 8/1932 | Youngren |
| 2,133,859 A | 10/1938 | Hawley |
| 2,398,915 A | 4/1946 | Bell |
| 2,443,363 A | 6/1948 | Townsend et al. |
| 2,489,870 A | 11/1949 | Dzus |
| 2,501,978 A | 3/1950 | Wichman |
| 2,561,550 A | 7/1951 | Wright |
| 2,737,835 A | 3/1956 | Herz |
| 3,463,148 A | 8/1969 | Treace |
| 3,534,731 A | 10/1970 | Muller ........................ 128/92 |
| 3,552,389 A | 1/1971 | Allgower et al. ............ 128/92 |
| 3,593,709 A | 7/1971 | Halloran ..................... 128/92 |
| 3,668,972 A | 6/1972 | Allgower et al. ............ 90/11 |
| 3,695,259 A | 10/1972 | Yost ........................... 128/92 |
| 3,716,050 A | 2/1973 | Johnston ..................... 128/92 |
| 3,741,205 A | 6/1973 | Markolf et al. .............. 128/92 |
| 3,779,240 A | 12/1973 | Kondo ........................ 128/92 |
| 3,807,394 A | 4/1974 | Attenborough ............. 128/92 |
| 4,219,015 A | 8/1980 | Steinemann ................ 128/92 |
| 4,338,921 A | 7/1982 | Harder et al. ............... 126/446 |
| 4,338,926 A | 7/1982 | Kummer et al. ............ 128/92 |
| 4,364,382 A | 12/1982 | Mennen ..................... 128/92 |
| 4,408,601 A | 10/1983 | Wenk ......................... 128/92 |
| 4,484,570 A | 11/1984 | Sutter et al. ................ 128/92 |

(Continued)

FOREIGN PATENT DOCUMENTS

DE    24 10 057 B1    7/1975

(Continued)

OTHER PUBLICATIONS

Notification of Transmittal of the International Search Report and the Written Opinion of the International Searching Authority, or the Declaration; International Application No. PCT/US2010/021553; International Filing Date Jan. 21, 2010, Mar. 24, 2010.

(Continued)

*Primary Examiner* — John J Wilson
(74) *Attorney, Agent, or Firm* — Baker Botts L.L.P.

(57) ABSTRACT

A plate for securing bones together includes an elongate spine having at least one groove spanning along a length of the spine parallel to a central axis of the spine, and a plurality of arms extending laterally from the spine, the plurality of arms comprising at least one arm on a first side of the spine and at least one arm on a second side of the spine.

21 Claims, 4 Drawing Sheets

U.S. PATENT DOCUMENTS

| | | | |
|---|---|---|---|
| 4,488,543 A | 12/1984 | Tornier | 128/92 |
| 4,493,317 A | 1/1985 | Klaue | 128/92 |
| 4,503,848 A | 3/1985 | Caspar et al. | 128/92 |
| 4,513,744 A | 4/1985 | Klaue | 128/92 |
| 4,565,193 A | 1/1986 | Streli | 128/92 |
| 4,573,458 A | 3/1986 | Lower | 128/92 |
| 4,651,724 A | 3/1987 | Berentey et al. | 128/92 |
| 4,683,878 A | 8/1987 | Carter | 128/92 |
| 4,794,918 A | 1/1989 | Wolter | 128/92 |
| 4,800,874 A | 1/1989 | David et al. | 128/92 |
| 4,838,252 A | 6/1989 | Klaue | 128/92 |
| 4,867,144 A | 9/1989 | Karas et al. | 128/92 |
| 4,955,886 A | 9/1990 | Pawluk | 606/69 |
| 4,959,065 A | 9/1990 | Arnett et al. | 606/69 |
| 5,002,544 A | 3/1991 | Klaue et al. | 606/69 |
| 5,006,120 A | 4/1991 | Carter | 606/69 |
| 5,015,248 A | 5/1991 | Burstein et al. | 606/74 |
| 5,015,249 A | 5/1991 | Nakao et al. | 606/142 |
| 5,021,056 A | 6/1991 | Hofmann et al. | 606/86 |
| 5,041,113 A | 8/1991 | Biedermann et al. | 606/61 |
| 5,053,036 A | 10/1991 | Perren et al. | 606/69 |
| 5,053,039 A | 10/1991 | Hofmann et al. | 606/87 |
| 5,057,111 A | 10/1991 | Park | 606/69 |
| 5,085,660 A | 2/1992 | Lin | 606/73 |
| 5,129,903 A | 7/1992 | Luhr et al. | 606/71 |
| 5,151,103 A | 9/1992 | Tepic et al. | 606/69 |
| 5,190,544 A | 3/1993 | Chapman et al. | 606/69 |
| 5,234,431 A | 8/1993 | Keller | 606/70 |
| 5,269,784 A | 12/1993 | Mast | 606/69 |
| 5,304,180 A | 4/1994 | Slocum | 606/69 |
| 5,330,535 A | 7/1994 | Moser et al. | 623/20 |
| 5,344,421 A | 9/1994 | Crook | 606/61 |
| 5,380,327 A | 1/1995 | Eggers et al. | 606/69 |
| 5,387,102 A | 2/1995 | Wagner et al. | 433/173 |
| 5,443,467 A | 8/1995 | Biedermann et al. | 606/65 |
| 5,474,553 A | 12/1995 | Baumgart | 606/71 |
| 5,486,176 A | 1/1996 | Hildebrand et al. | 606/71 |
| 5,487,741 A | 1/1996 | Maruyama et al. | 606/60 |
| 5,501,684 A | 3/1996 | Schlapfer et al. | 606/73 |
| 5,531,746 A | 7/1996 | Errico et al. | 606/61 |
| 5,549,612 A | 8/1996 | Yapp et al. | 606/69 |
| 5,578,034 A | 11/1996 | Estes | 606/61 |
| 5,591,166 A | 1/1997 | Bernhardt et al. | 606/61 |
| 5,601,553 A | 2/1997 | Trebing et al. | 606/61 |
| 5,603,713 A | 2/1997 | Aust et al. | 606/61 |
| 5,607,426 A | 3/1997 | Ralph et al. | 606/61 |
| 5,607,428 A | 3/1997 | Lin | 606/69 |
| 5,620,448 A | 4/1997 | Puddu | 606/87 |
| 5,643,265 A | 7/1997 | Errico et al. | 606/70 |
| 5,662,655 A | 9/1997 | Laboureau et al. | 606/75 |
| 5,674,222 A | 10/1997 | Berger et al. | 606/69 |
| 5,676,667 A | 10/1997 | Hausman | 606/69 |
| 5,681,311 A | 10/1997 | Foley et al. | 606/61 |
| 5,709,686 A | 1/1998 | Talos et al. | 606/69 |
| 5,725,588 A | 3/1998 | Errico et al. | 623/22 |
| 5,733,287 A | 3/1998 | Tepic et al. | 606/69 |
| 5,735,853 A | 4/1998 | Olerud | 606/71 |
| 5,741,258 A | 4/1998 | Klaue et al. | 606/70 |
| 5,746,742 A | 5/1998 | Runciman et al. | 606/69 |
| 5,749,872 A | 5/1998 | Kyle et al. | 606/69 |
| 5,749,875 A | 5/1998 | Puddu | 606/87 |
| 5,810,823 A | 9/1998 | Klaue et al. | 606/69 |
| 5,931,838 A | 8/1999 | Vito | 606/61 |
| 5,938,664 A | 8/1999 | Winquist et al. | 606/69 |
| 5,951,558 A | 9/1999 | Fiz | 606/70 |
| 5,954,722 A | 9/1999 | Bono | 606/61 |
| 5,964,762 A | 10/1999 | Biedermann et al. | 606/69 |
| 6,001,099 A | 12/1999 | Huebner | 606/69 |
| 6,093,188 A | 7/2000 | Murray | 606/69 |
| 6,117,173 A | 9/2000 | Taddia et al. | 623/16.11 |
| 6,139,550 A | 10/2000 | Michelson | 606/69 |
| 6,152,927 A | 11/2000 | Farris et al. | 606/69 |
| 6,183,475 B1 | 2/2001 | Lester et al. | 606/69 |
| 6,193,721 B1 | 2/2001 | Michelson | 606/70 |
| 6,206,881 B1 | 3/2001 | Frigg et al. | 606/69 |
| 6,224,602 B1 | 5/2001 | Hayes | 606/69 |
| 6,228,085 B1 | 5/2001 | Theken et al. | 606/61 |
| 6,235,032 B1 | 5/2001 | Link | 606/69 |
| 6,235,033 B1 | 5/2001 | Brace et al. | 606/69 |
| 6,235,034 B1 | 5/2001 | Bray | 606/71 |
| 6,241,731 B1 | 6/2001 | Fiz | 606/65 |
| 6,261,291 B1 | 7/2001 | Talaber et al. | 606/69 |
| 6,302,883 B1 | 10/2001 | Bono | 606/69 |
| 6,309,393 B1 | 10/2001 | Tepic et al. | 606/69 |
| 6,315,779 B1 | 11/2001 | Morrison et al. | 606/69 |
| 6,322,562 B1 | 11/2001 | Wolter | 606/69 |
| 6,342,055 B1 | 1/2002 | Eisermann et al. | 606/69 |
| 6,348,052 B1 | 2/2002 | Sammarco | 606/69 |
| 6,383,186 B1 | 5/2002 | Michelson | 606/69 |
| 6,413,259 B1 | 7/2002 | Lyons et al. | 606/69 |
| 6,454,770 B1 | 9/2002 | Klaue | 606/69 |
| 6,503,250 B2 | 1/2003 | Paul | 606/69 |
| 6,527,776 B1 | 3/2003 | Michelson | 606/70 |
| 6,533,789 B1 | 3/2003 | Hall, IV et al. | 606/69 |
| 6,575,975 B2 | 6/2003 | Brace et al. | 606/69 |
| 6,592,586 B1 * | 7/2003 | Michelson | 606/71 |
| 6,595,993 B2 | 7/2003 | Donno et al. | 606/71 |
| 6,602,255 B1 | 8/2003 | Campbell et al. | 606/69 |
| 6,623,486 B1 | 9/2003 | Weaver et al. | 606/69 |
| 6,669,701 B2 | 12/2003 | Steiner et al. | 606/69 |
| 6,682,531 B2 | 1/2004 | Winquist et al. | 606/69 |
| 6,695,846 B2 | 2/2004 | Richelsoph et al. | 606/71 |
| 6,719,759 B2 | 4/2004 | Wagner et al. | 606/69 |
| 6,755,832 B2 | 6/2004 | Happonen et al. | 606/69 |
| 6,755,833 B1 | 6/2004 | Paul et al. | 606/70 |
| 6,821,278 B2 | 11/2004 | Frigg et al. | 606/69 |
| 6,890,334 B2 | 5/2005 | Brace et al. | 606/69 |
| 6,945,973 B2 | 9/2005 | Bray | 606/61 |
| 7,001,389 B1 | 2/2006 | Navarro et al. | 606/71 |
| 7,128,744 B2 | 10/2006 | Weaver et al. | 606/69 |
| 7,175,624 B2 | 2/2007 | Konieczynski et al. | 606/71 |
| 7,179,260 B2 | 2/2007 | Gerlach et al. | 606/69 |
| 7,273,481 B2 | 9/2007 | Lombardo et al. | 606/69 |
| 7,288,095 B2 | 10/2007 | Baynham et al. | 606/69 |
| 7,309,340 B2 | 12/2007 | Fallin et al. | 606/104 |
| 7,311,712 B2 | 12/2007 | Dalton | 606/71 |
| 7,331,961 B2 | 2/2008 | Abdou | 606/71 |
| 2001/0037112 A1 | 11/2001 | Brace et al. | 606/69 |
| 2002/0082606 A1 | 6/2002 | Suddaby | 606/96 |
| 2003/0040749 A1 | 2/2003 | Grabowski et al. | 606/71 |
| 2003/0078583 A1 | 4/2003 | Biedermann et al. | 606/69 |
| 2003/0187440 A1 | 10/2003 | Richelsoph et al. | 606/61 |
| 2003/0187442 A1 | 10/2003 | Richelsoph et al. | 606/70 |
| 2003/0199876 A1 | 10/2003 | Brace et al. | 606/69 |
| 2004/0015169 A1 | 1/2004 | Gause | 606/63 |
| 2004/0034354 A1 | 2/2004 | Paul | 606/70 |
| 2004/0059334 A1 | 3/2004 | Weaver et al. | 606/69 |
| 2004/0059335 A1 | 3/2004 | Weaver et al. | 606/69 |
| 2004/0087951 A1 | 5/2004 | Khalili | 606/69 |
| 2004/0102777 A1 * | 5/2004 | Huebner | 606/69 |
| 2004/0127901 A1 | 7/2004 | Huebner et al. | 606/69 |
| 2004/0215192 A1 * | 10/2004 | Justis et al. | 606/61 |
| 2005/0065521 A1 | 3/2005 | Steger et al. | 606/69 |
| 2005/0070904 A1 | 3/2005 | Gerlach et al. | 606/69 |
| 2005/0080421 A1 | 4/2005 | Weaver et al. | 606/69 |
| 2005/0131413 A1 | 6/2005 | O'Driscoll et al. | 606/73 |
| 2005/0234455 A1 | 10/2005 | Binder et al. | 606/69 |
| 2005/0240185 A1 * | 10/2005 | Boomer et al. | 606/69 |
| 2006/0015102 A1 | 1/2006 | Toullec et al. | 606/69 |
| 2006/0036249 A1 | 2/2006 | Baynham et al. | 606/69 |
| 2006/0173459 A1 | 8/2006 | Kay et al. | 606/69 |
| 2006/0235396 A1 | 10/2006 | Sanders et al. | 606/69 |
| 2006/0235397 A1 | 10/2006 | Sanders et al. | 606/69 |
| 2006/0241592 A1 | 10/2006 | Myerson et al. | 606/61 |
| 2006/0241607 A1 | 10/2006 | Myerson et al. | 606/69 |
| 2006/0241608 A1 | 10/2006 | Myerson et al. | 606/69 |
| 2007/0055253 A1 | 3/2007 | Orbay et al. | 606/69 |
| 2007/0088360 A1 | 4/2007 | Orbay et al. | 606/69 |
| 2007/0123880 A1 | 5/2007 | Medoff | 606/69 |
| 2007/0162020 A1 | 7/2007 | Gerlach et al. | 606/69 |
| 2007/0233115 A1 | 10/2007 | Sixto et al. | 606/69 |
| 2007/0239163 A1 | 10/2007 | Strnad et al. | 606/72 |
| 2007/0260244 A1 | 11/2007 | Wolter | 606/60 |
| 2007/0276383 A1 | 11/2007 | Rayhack | 606/69 |
| 2007/0276386 A1 | 11/2007 | Gerlach et al. | 606/72 |

| | | | |
|---|---|---|---|
| 2008/0015591 A1 | 1/2008 | Castaneda et al. | 606/69 |
| 2008/0015592 A1 | 1/2008 | Long et al. | 606/69 |
| 2008/0154310 A1* | 6/2008 | White et al. | 606/280 |

FOREIGN PATENT DOCUMENTS

| | | |
|---|---|---|
| EP | 0 024 635 A1 | 3/1981 |
| GB | 2 331 244 A | 5/1999 |
| GB | 2 451 187 A | 1/2009 |
| WO | WO 2004/045389 A2 | 6/2004 |
| WO | WO 2004/045455 A2 | 6/2004 |

OTHER PUBLICATIONS

"An Improved Bone Clamp and a Plate for Internal Fixation of Fractures", by Jean Verbrugge; *J Bone Joint Surg Am.* 1946; 28: 174-175, 1946.

"Locked Plating System for Reconstructive Rearfoot Surgery", Darco MRS; Wright Medical Technology, Inc., 2007.

* cited by examiner

MULTIPLE BONE FUSION PLATE

TECHNICAL FIELD

The present disclosure relates to a device for securing bones together, and more particularly, to a multiple bone fusion plate.

BACKGROUND

When performing certain medical procedures, such as restoring the natural geometry of an arch of a foot that has collapsed, a surgeon may have a need to affix multiple bones together in a particular configuration in order to reconstruct one or more failed or failing joints of the arch. One way to achieve this objective is to attach the bones of the joint structure to a plate that holds the bones in a configuration similar to their natural positions until the joints structure heals, such as for example by fusing together.

SUMMARY

The present disclosure relates generally to an orthopedic device. More specifically, the present disclosure relates to a plate for securing multiple bones together and a method for using the same.

In particular embodiments, a plate for securing bones together may include an elongate spine having at least one groove spanning along a length of the spine parallel to a central axis of the spine. The plate may further include a plurality of arms extending laterally from the spine, the plurality of arms including at least one arm on a first side of the spine and at least one arm on a second side of the spine.

Depending upon design, the at least one arm on the first side of the spine and the at least one arm on the second side of the spine may each include an attachment point for attaching the arms to a bone. As an example and not by way of limitation, the attachment point may include a screw hole defined by an inner surface configured to engage the head of one of a plurality of bone screws. As another example and not by way of limitation, the attachment point may include a threaded screw hole defined by a threaded inner surface configured to lockably engage one of a plurality of locking bone screws. In particular embodiments, the at least one arm on the first side of the spine and the at least one arm on the second side of the spine may each include a rigid, rounded tab extending laterally from the spine perpendicular to the central axis of the spine.

In particular embodiments, a first surface of the spine may include a thickened ridge spanning along a length of the spine parallel to the central axis of the spine. The at least one groove may be included on a second surface, opposite the first surface. The thickened ridge may include, for example, a generally smooth, elevated ridge of material symmetrically distributed about the central axis of the spine which may span from the first end of the spine to the second end of the spine. The thickened ridge may be thickest in the center of the spine and taper off in thickness as the thickened ridge extends laterally toward the plurality of arms. The at least one groove may include a pair of recessed channels symmetrically distributed about the central axis of the spine which span from the first end of the spine to the second end of the spine.

In particular embodiments, the plate may include a cross-sectional curvature in a plane perpendicular to the central axis, and compression of the at least one groove may draw the at least one arm on the first side of the spine toward the at least one screw hole on the second side of the spine and increase the cross-sectional curvature of the spine.

Depending upon design, compression of the at least one groove may also increase the axial stiffness of the plate along the central axis of the plate.

In particular embodiments, the plate may include a memory shape material operable to compress the at least one groove when the plate is heated above a transformation temperature of the memory shape material.

In particular embodiments, the plate may include one or more screw holes disposed along the spine.

In particular embodiments, the plate may be curved along the central axis to approximate the geometry of a joint structure.

A method for securing bones together may include attaching a plate to a first bone and a second bone. The plate may include an elongate spine comprising at least one groove spanning along a length of the spine parallel to a central axis of the spine, and a plurality of arms extending laterally from the spine. The plurality of arms may include at least one arm on a first side of the spine and at least one arm on a second side of the spine.

In particular embodiments, the at least one arm on the first side of the spine and the at least one arm on the second side of the spine may each include an attachment point that includes a screw hole defined by an inner surface configured to lockably engage a head of one of a plurality of bone screws. The step of attaching may include screwing a bone screw into the screw hole on the at least one arm on the first side of the spine or the at least one arm on the second side of the spine until the bone screw engages the screw hole.

In particular embodiments, the method may further include compressing the at least one groove to draw the at least one screw hole on the first side of the spine toward the at least one screw hole on the second side of the spine.

In particular embodiments, the compressing step may occur after the attaching step, or the compressing step may occur before the attaching step.

In particular embodiments, the plate may include a memory shape material operable to compress the at least one groove when the plate is heated above a transformation temperature of the memory shape material, and the method may further include the step of mechanically deforming the plate such that the memory shape material is operable to compress the at least one groove once the plate is heated above the transformation temperature.

Particular embodiments of the present disclosure may provide a number of technical advantages. For example, compression of the grooves along the spine of the plate may raise the section modulus of the plate along the spine. This technical advantage increases the load that the spine of the plate may support. Furthermore, by compressing the grooves after the plate has been implanted in a patient, a surgeon may tighten the geometry of the bony structure attached to the plate by drawing each of the bones attached to the plate together, toward the central axis of the plate. This technical advantage may enable a surgeon to use the plate to tighten an entire joint structure at once, rather than having to manipulate multiple bones individually. Additionally, when the plate is mounted on the compression side of a joint (e.g., to the dorsal side of the medial column or the lateral column of a foot), compression of the grooves may deflect the arms of the plate (and the bones attached thereto) slightly downward, toward the tension side of the joint. This technical advantage may aid the plate in drawing the bones of the joint closer together, for example, to promote fusion of the joint structure. Particular embodiments of the plate may include a thickened ridge of material disposed along the central axis of the spine that may increase the bending stiffness of the plate, yet another technical advantage.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following descriptions, taken in conjunction with the accompanying drawings, in which.

DETAILED DESCRIPTION OF EXAMPLE EMBODIMENTS

A Charcot deformity, also called Charcot joint or neuropathic joint, is a progressive condition of the musculoskeletal system that is characterized by joint dislocations, pathologic fractures, and debilitating deformities. This disorder results in progressive destruction of bone and soft tissues at weight-bearing joints. In its most severe form, a Charcot deformity may cause significant disruption of the bony architecture surrounding the affected joint(s). Although a Charcot deformity may occur at any joint, it most frequently occurs in the lower extremities such as in the foot.

A Charcot deformity may arise as a complication of a systemic disease, such as diabetes, that causes neuropathy (e.g., nerve damage) of the foot. When neuropathy is present, a person's ability to sense pain in the affected area (e.g., the foot) is often lost or impaired. Further symptoms of neuropathy include weakening of the bones and loss of adequate muscle strength to support the joint structure of the foot.

Due to a lack of feeling caused by the neuropathy and a general weakening of structure of the foot, minor traumas such sprains or stress fractures may develop and go undetected and untreated for extended periods of time, leading to further complications in the affected foot such as slackness of the ligaments, dislocation of the joints, collapse of the arch, damage to bones and cartilage, valgus deviation, and ultimately, permanent deformity.

Figure 1:
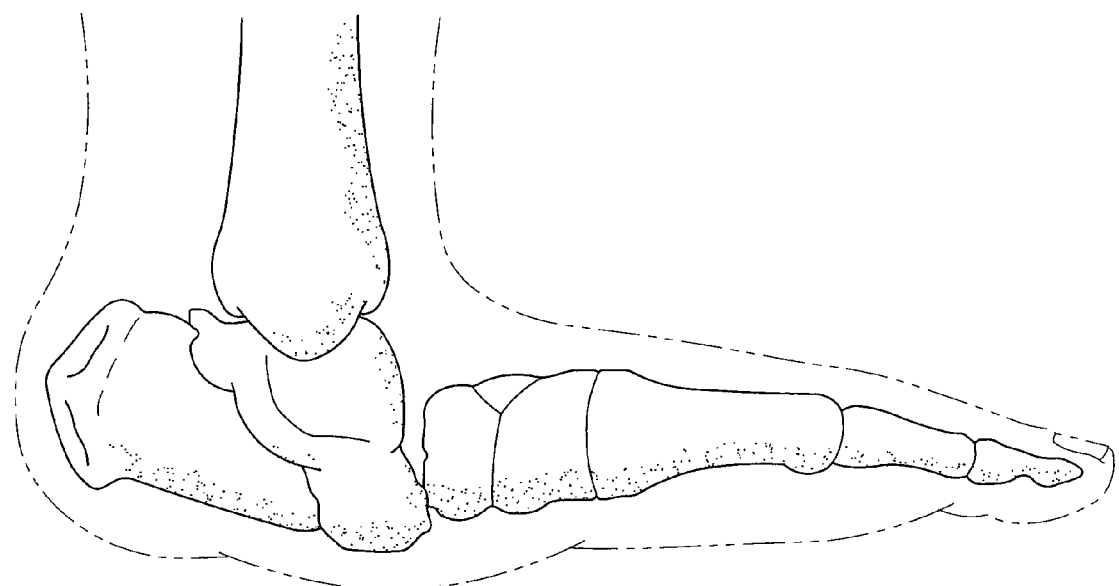
FIG. 1 illustrates a foot in which the Navicular-Cuneiform joint has failed, causing the arch of the foot to collapse.

In a typical scenario, a person having neuropathy in the foot may continue to walk on it regularly, despite having weakened bones and ligaments. Since the bones, tendons, and muscles in the affected area are often weak enough to fail a result of minor trauma (such as a long walk), continued walking may eventually change the shape of the foot. As the disorder progresses, the arch may collapse (e.g., the Navicular-Cuneiform joint and other joints of the foot fail) and the foot may take on a convex shape (see FIG. 1), giving it a rocker-bottom appearance. FIG. 1 illustrates a severe embodiment of a Charcot deformity.

In many cases, the symptoms of a Charcot deformity, if detected in its early stages, may be treated using conservative measures such as immobilization of the foot, followed by custom shoes and inserts and activity modification. However, in advanced cases such as illustrated in FIG. 1, conservative measures may be ineffective, and surgery may be required. Where surgery is required, a multiple bone fusion plate may attached to the dorsum (e.g., the top side) of the foot to reconstruct the foot's arch and to act as a load bearing member which holds the bones of the joint structure in place while the joint structure heals.

A multiple bone fusion plate may be used to fuse either the lateral column or the medial column of the foot. Most frequently, however, the multiple bone fusion plate is used for fusion of the medial column. Typically fused bones of the medial column include a combination of the talus, the navicular, the cuneiforms, and the metatarsals.

Figure 2:
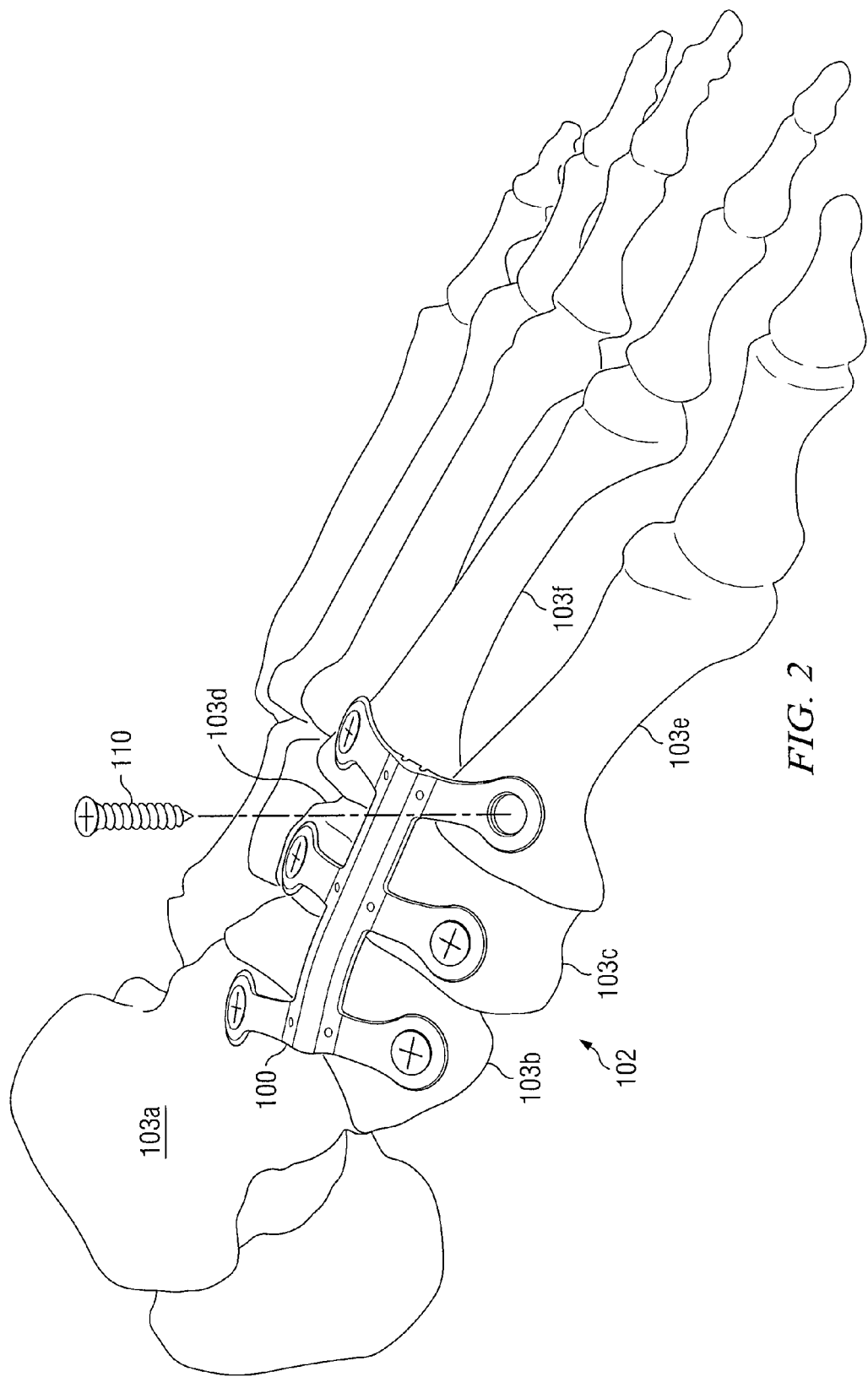
FIG. 2 illustrates an example embodiment of a multiple fusion plate being secured over the failed Navicular-Cuneiform joint of FIG. 1 in order to reconstruct the arch of the foot.
Figure 3:
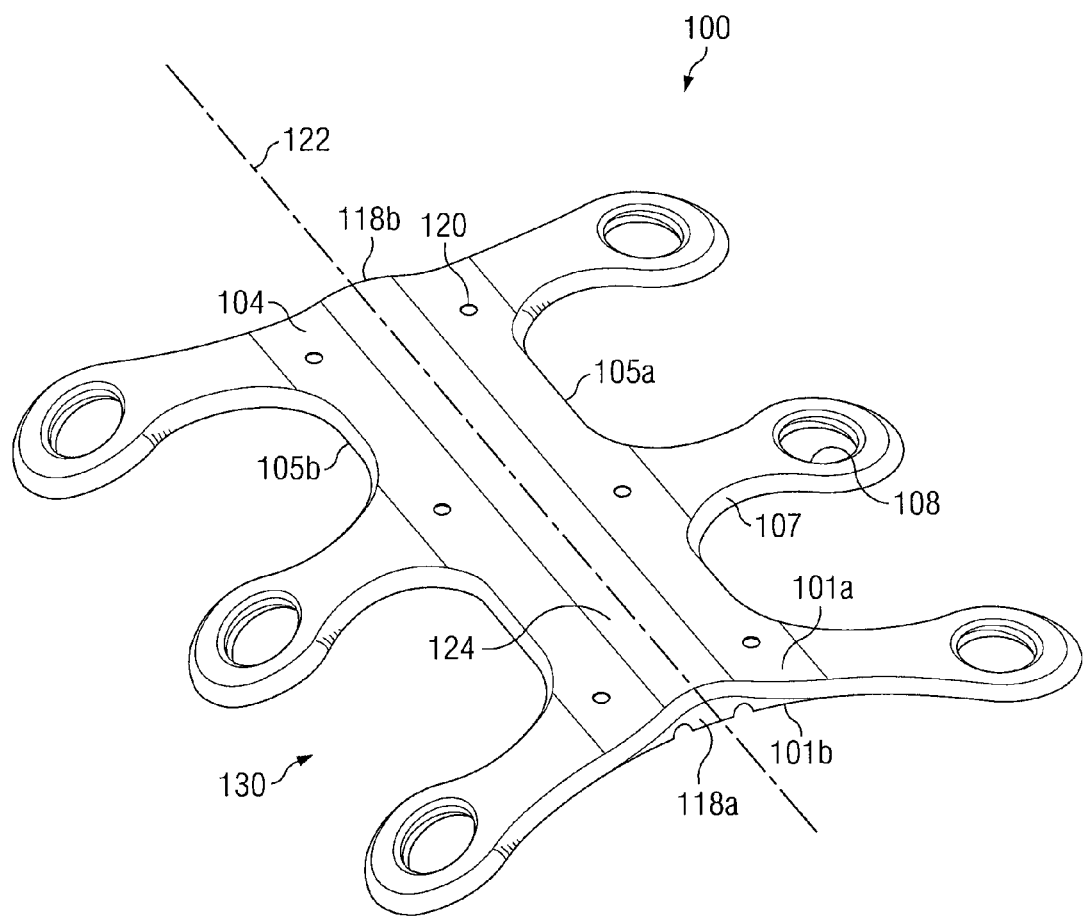
FIG. 3 illustrates an external view of the top surface of the multiple fusion plate of FIG. 2.
Figure 4:
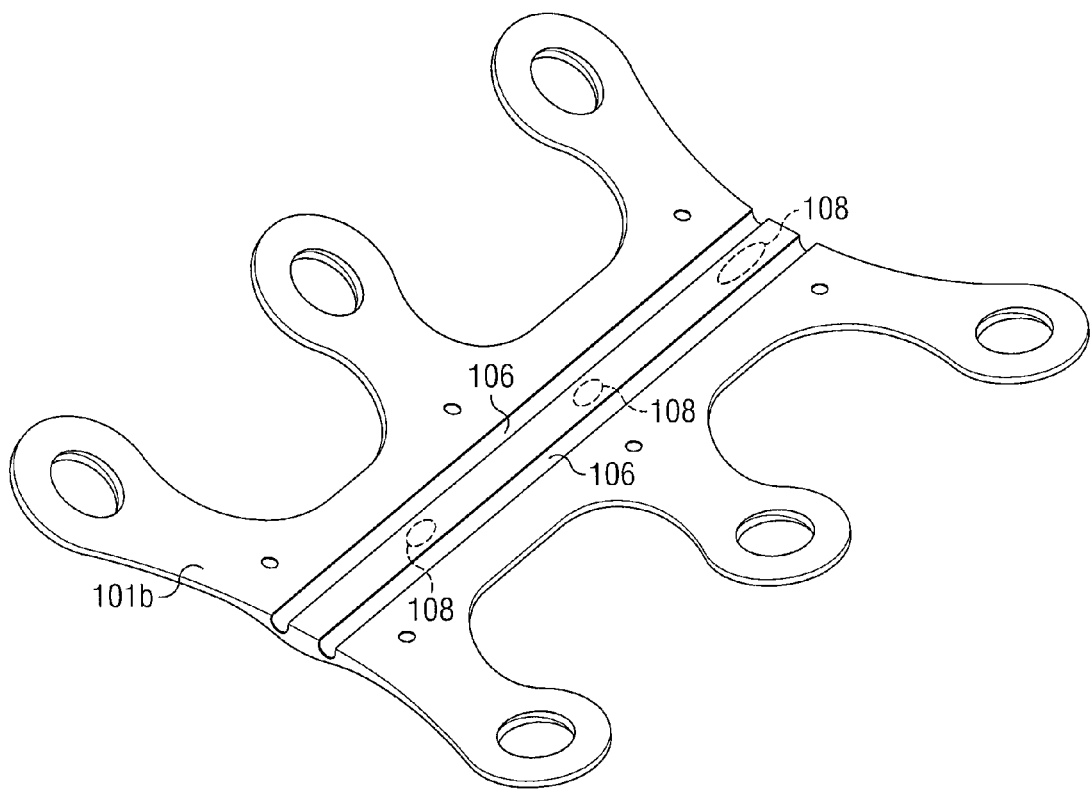
FIG. 4 illustrates an external view of the bottom surface of the multiple fusion plate of FIG. 2.

FIGS. 2-4 illustrate a multiple fusion plate 100 in accordance with a particular embodiment of the present disclosure. More particularly, FIG. 2 illustrates multiple fusion plate 100 being secured to a foot over a collapsed or weakened joint structure 102 in order to reconstruct or approximate the natural geometry of joint structure 102; FIG. 3 illustrates an external view of the top surface 101a of multiple fusion plate 100; and FIG. 4 illustrates an external view of the bottom surface 101b of multiple fusion plate 100.

For reference purposes, multiple fusion plate 100 may be referred to as having a top surface 101a intended to face away from the bones of joint structure 102 and a bottom surface 101b intended to face toward the bones of joint structure 102 (e.g., to be placed upon the bones of joint structure 102). Though particular features of multiple fusion plate 100 may be explained using such intended placement as a point of reference, this method of explanation is not meant to limit the scope of the present disclosure to any particular configuration of multiple fusion plate 100.

As shown in FIG. 2, multiple fusion plate 100 is being used to reconstruct a failed joint structure 102 of a human foot. In particular, FIG. 2 illustrates multiple fusion plate 100 being coupled to the talus 103a, navicular 103b, medial cunieform 103c, intermediate cunieform 103d, first metatarsal 103e, and second metatarsal 103f in order restore the Navicular-Cuneiform joint show collapsed in FIG. 1 as a result of neuropathy. However, one of ordinary skill in the art will appreciate that particular embodiments of multiple fusion plate 100 may be applied equally as well to reconstruct the natural geometry of virtually any joint structure 102 in the body (e.g., in the foot, hand, or spine) without departing from the scope of the present disclosure. Additionally, multiple fusion plate 100 may be used in other applications such as reconstructing a fractured bone or aligning and attaching a bone to a synthetic element, such as a medical implant. To facilitate the process of aligning joint structure 102, particular embodiments of multiple fusion plate 100 may be configured to approximate the natural geometry of the joint or joints being reconstructed. Furthermore, a surgeon may intra-operatively contour multiple fusion plate 100, such as for example, by bending the spine of multiple fusion plate 100 to approximate the geometry of joint structure 102.

In a typical scenario, a surgeon may use multiple fusion plate 100 to reconstruct joint structure 102 using the following procedure. The surgeon may begin by creating an incision over joint structure 102 to expose the bones of joint structure 102. The surgeon may then align the bones of joint structure 102 into a desired configuration (e.g., the natural configuration joint structure 102) and secure multiple fusion plate 100 to the bones of joint structure 102 to hold them in position using, for example, one or more locking bone screws 110. After multiple fusion plate 100 has been affixed to the bones of joint structure 102, the incision may be closed, and joint structure 102 may be further immobilized by applying a cast, splint, or other immobilization fixture around joint structure 102. Once joint structure 102 has healed, multiple fusion plate 100 may optionally be removed by means of a minor surgical procedure, leaving the patient to function normally.

FIG. 3 illustrates an external view of the top surface 101*a* of multiple fusion plate 100. In particular embodiments, multiple fusion plate 100 may be characterized by a substantially thin, elongate construction, having a top surface 101*a* and a bottom surface 101*b* (collectively surfaces 101). Multiple fusion plate 100 may generally include an elongate spine 104 having a first side 105*a* and a second side 105*b* (collectively sides 105) and a plurality of arms 107 extending laterally from spine 104. Each arm 107 may further include one or more attachment points 108 for attaching multiple fusion plate 100 to a bone. For example, in a typical procedure, each arm 107 may be attached to a different bone of joint structure 102 by means of its own attachment point 108. As mentioned above, once multiple fusion plate 100 is attached to the bones of joint structure 102, multiple fusion plate 100 may act as a load bearing member that holds the bones of joint structure 102 in place while joint 102 heals. Once joint 102 has properly healed, weight may be placed on joint structure 102 during activities such as running, walking, or standing.

Arms 107 may serve as the primary mechanism for attaching multiple fusion plate 100 to the bones of joint structure 102. Each arm 107 may be any type of rigid lateral extension from spine 104 capable of supporting a bone in a fixed position relative to spine 104. As an example and not by way of limitation, each arm 107 may be a rigid rounded tab extending laterally from spine 104 perpendicular to the central axis 122 of spine 104. Depending upon design, each arm 107 may be separated from the next by a gap 130, which may enable a surgeon to independently contour each arm 107 to a desired position (e.g., to conform arms 107 to match the bony geometry of joint structure 102). Furthermore, each arm 107 may be relatively thinner than spine 104 to reduce the mechanical force needed to contour arms 107 up or down relative to spine 104. This thinning of arms 107 may confer a number of advantages over plates having uniform thickness, such as for example, providing a surgeon with the ability to easily contour arms 107 to a desired position, reducing the overall thickness of the plate, lessening the chance of uncomfortable impingement on the surrounding soft tissue, and reducing patient palpation and visualization of multiple fusion plate 100. Once an arm 107 has been contoured to the desired position, it may be affixed to a bone using an attachment point 108.

Each arm 107 may include one or more attachment points 108. An attachment point 108 may be any mechanism or fixture operable to serve as a rigid point of attachment between an arm 107 and a bone. As one example and not by way of limitation, an attachment point 108 may be an unthreaded screw hole in multiple fusion plate 100 configured to accept a bone screw. As another example an not by way of limitation, an attachment point 108 may be a threaded screw hole in arm 107 configured to provide a locking interface between a locking screw 110 and multiple fusion plate 100. To accomplish this locking interface, the under side of the head of locking screw 110 may include threads that interfere with the threading on the inside of the threaded screw hole to lock locking screw 110 into multiple fusion plate 100 once locking screw 110 is screwed into a bone through multiple fusion plate 100. Consequently, once locking screw 110 is screwed into a bone through the threaded screw hole, locking screw 110 may be prevented from loosening or backing out of the bone. An example system for providing a locking interface between a screw hole and a locking screw is presented in U.S. Provisional Application No. 61/106,511, entitled, "Angulated Locking Plate/Screw Interface." As another example and not by way of limitation, an attachment point 108 may be any type of clip or clamp included on arm 107 operable to rigidly affix arm 107 to a bone. In particular embodiments, multiple fusion plate 100 may further include screw holes or slots in spine 104 to serve as additional attachment points 108 for affixing multiple fusion plate 100 to a bone. One of ordinary skill in the art will appreciate that the above-described embodiments of attachment point 108 were presented for the sake of explanatory clarification and will further appreciate that the present disclosure contemplates attachment point 108 being any suitable mechanism or fixture operable to serve as a rigid point of attachment between an arm 107 and a bone.

Spine 104 may generally define the central portion of multiple fusion plate 100 and may be any fixture capable of rigidly connecting arms 107 together along the length of multiple fusion plate 100. As an example and not by way of limitation, spine 104 may include a contiguous linear or curvilinear section of multiple fusion plate 100 spanning from the first end 118*a* of multiple fusion plate 100 to the second end 118*b* of multiple fusion plate 100 parallel to the central axis 122 (e.g., the neutral axis) of multiple fusion plate 100. Since multiple fusion plate 100 is generally elongate, the length of spine 104 along central axis 122 is greater than the width of spine 104 perpendicular to central axis 122.

To increase the strength of multiple fusion plate 100, spine 104 may include a number of features that increase the axial stiffness of multiple fusion plate 100 along central axis 122. For example, in particular embodiments, spine 104 may include a thickened ridge 124 of material symmetrically distributed about central axis 122 that traverses the entire length of multiple fusion plate 100 parallel to central axis 122. To keep thickened ridge 124 from interfering with the bony geometry underlying multiple fusion plate 100, thickened ridge 124 typically protrudes from the top surface 101*a* of multiple fusion plate 100, leaving bottom surface 101*b* generally free of obstructions that might protrude into the bony geometry of joint structure 102. In a typical design, thickened ridge 124 is a generally smooth, rounded elevation in multiple fusion plate 100 having its greatest thickness in the center of multiple fusion plate 100 (e.g., along central axis 122) and gradually decreasing in thickness as one moves laterally away from central axis 122 toward arms 107. Including thickened ridge 124 in multiple fusion plate 100 may confer a number of advantages over plates of uniform thickness, one of which, is the ability to efficiently increase the bending stiffness of multiple fusion plate 100 along central axis 122 without adding thickness to the entire plate.

As another mechanism for increasing the axial stiffness of multiple fusion plate 100, particular embodiments of multiple fusion plate 100 may include one or more compression grooves 106 in spine 104 that may be compressed (e.g., pinched together) to increase the bending stiffness of spine 104.

FIG. 4 illustrates an external view of two parallel compression grooves 106 included on the bottom surface 101*b* of multiple fusion plate 100 in accordance with a particular embodiment of the present disclosure. Each compression groove 106 may be any type of recessed channel in spine 104 running generally parallel to central axis 122. By pinching compression grooves 106 together in a localized area or along the entire length of multiple fusion plate 100, a surgeon may either pre-operatively or intra-operatively increase the stiffness of multiple fusion plate 100. Depending upon design, if screw holes or slots are included in spine 104, they may reside between compression grooves 106, as indicated by the dashed circles of FIG. 4.

When a sufficient amount compressive force is applied to compression grooves 106, such as for example, by squeezing sides 105 together with a pair of pliers, compression grooves 106 may collapse on themselves, driving the overlying portion of spine 104 upward. This elevation of spine 104 may increase the section modulus of multiple fusion plate 100, making multiple fusion plate 100 stiffer in the direction of compression grooves 106 (e.g., along central axis 122). Thus, including compression grooves 106 in multiple fusion plate 100, may confer a number of advantages over plates where the axial stiffness of the plate is primarily a function of the material thickness, one of which, is the ability to increase the bending stiffness of multiple fusion plate 100 along central axis 122 without adding more material to the plate.

In a typical design, compression grooves 106 may reside on the bottom surface 101b of multiple fusion plate 100, opposite thickened ridge 124, and may traverse the entire length of multiple fusion plate 100, parallel to central axis 122. Although the pictured embodiment illustrates multiple fusion plate 100 as including two semi-circular compression grooves 106 symmetrically distributed about central axis 122, the present disclosure contemplates including any suitable number and distribution of compression grooves 106 about central axis 122, having any suitable cross-sectional shape.

In particular embodiments, multiple fusion plate 100 may comprise one or more positioning holes 120 or positioning slots that may be used to position multiple fusion plate 100 relative to the bones of joint structure 102. To position multiple fusion plate 100 using a positioning hole 120, a surgeon may insert a guide wire such as a Kirschner Wire ("K-wire") into one of the bones of joint structure 102, after which the surgeon may position multiple fusion plate 100 on the bone by inserting the K-wire through positioning hole 120 and sliding multiple fusion plate 100 down onto the bone. Additionally, the surgeon may rotate multiple fusion plate 100 about the K-wire using positioning hole 120 to achieve a desired orientation of multiple fusion plate 100 relative to the bone. Once multiple fusion plate 100 has been properly positioned, the surgeon may secure multiple fusion plate 100 to the bone, temporarily for example, by inserting another K-wire into another one of positioning holes 120, or more permanently, using attachment points 108.

As briefly mentioned above, a surgeon may compress grooves 106 together either before or after affixing multiple fusion plate 100 to the bones of joint structure 102. In the latter case, once multiple fusion plate 100 has been rigidly affixed to the bones of joint structure 102 (e.g., using attachment points 108), compressing grooves 106 may result in a number of beneficial enhancements to joint structure 102. In particular, by compressing grooves 106 together after affixing multiple fusion plate 100 to the bones of joint structure 102, a surgeon may draw one or more of the bones connected to multiple fusion plate 100 inward, toward central axis 122, thereby tightening up the bony geometry of joint structure 102 and increasing the fusion effectiveness of the fused joint(s). Furthermore, the compression of grooves 106 may also increase the cross-sectional curvature of multiple fusion plate 100 in the plane perpendicular to central axis 122.

In cases where multiple fusion plate 100 is mounted to the compression side of joint structure 102, the increase in the cross-sectional curvature of multiple fusion plate 100 caused by the compression of grooves 106 may result in a deflection of the bones connected to arms 107 toward the tension side of joint structure 102, which may promote fusion of joint structure 102. For example, if multiple fusion plate 100 were affixed to the dorsal side of the Navicular-Cuneiform joint as illustrated in FIG. 2, the compression of grooves 106 would result in the attached bones of the medial column (e.g., the talus 103a, the navicular 103b, the medial cunieform 103c, the intermediate cunieform 103d, the first metatarsal 103e, and the second metatarsal 103f) not only being drawn inward toward central axis 122, but also being deflected downward toward the plantar aspect of the foot (e.g., the sole of the foot). The downward deflection of those bones caused by the compression of grooves 106 may help to counteract the tension forces exerted on the sole of the foot during activities such as running or walking, thus enabling the foot to function properly after joint 102 has healed.

Depending upon design, multiple fusion plate 100 may be formed from any material or combination of materials suitable for forming medical implants. Such materials may have high strength-to-weight ratios and be inert to human body fluids. As an example and not by way of limitation, multiple fusion plate 100 may be formed from unalloyed titanium. Titanium may provide several benefits as a material for multiple fusion plate 100 such as being relatively lightweight, providing adequate strength for withstanding forces typically experienced by a fusion plate, and being visible in radiographs of the implant region.

As another example and not by way of limitation, multiple fusion plate 100 may be created from a shape memory material such as NITINOL (e.g. a Nickel-Titanium alloy). In general, a shape memory material, if deformed while heated above a certain temperature (e.g., its transformation temperature), has the ability to return to its undeformed shape when cooled below its transformation temperature and then to return to its deformed shape when reheated above its transformation temperature. It has also been found that shape memory materials are capable of generating significant force when changing shape. Consequently, by creating multiple fusion plate 100 out of a shape memory material having a transformation temperature below body temperature (e.g., below 98.6 degrees Farenheight), it may be possible to use the shape memory properties of the shape memory material to compress grooves 106 once multiple fusion plate 100 has been implanted in a patient.

To achieve this type of compression, a surgeon, before implanting multiple fusion plate 100 into a patient, may heat multiple fusion plate 100 above its transformation temperature and compress grooves 106 using a pair of pliers. The surgeon may then cool multiple fusion plate 100 below its transformation temperature, causing multiple fusion plate 100 to return to its original shape where grooves 106 are in their uncompressed state. The surgeon may then affix multiple fusion plate 100 to the bones of joint structure 102 using the surgical procedures described above. Once multiple fusion plate 100 has been secured to joint structure 102, the patient's body temperature may heat multiple fusion plate 100 above its transformation temperature, causing grooves 106 to compress due to the shape memory properties of the shape memory material. Consequently, by creating multiple fusion plate 100 out of a shape memory material having a transformation temperature below body temperature, it is possible use a patient's body heat to activate the shape memory properties of the shape memory material to compress groove 106. This may eliminate the need for the surgeon to mechanically compress grooves 106 after securing multiple fusion plate 100 to joint structure 102.

Although the present disclosure has been described in several embodiments, a myriad of changes, substitutions, and modifications may be suggested to one skilled in the art, and it is intended that the present disclosure encompass such changes, substitutions, and modifications as fall within the scope of the present appended claims.

What is claimed is:

1. A plate for securing bones together, comprising:
an elongate spine comprising at least one groove spanning along a length of the spine parallel to a central axis of the spine, wherein:
a first surface of the spine comprises a thickened ridge spanning along a length of the spine parallel to the central axis of the spine; and
a second surface, opposite the first surface, comprises the at least one groove; and
a plurality of arms extending laterally from the spine, the plurality of arms comprising at least one arm on a first side of the spine and at least one arm on a second side of the spine.

2. The plate of claim 1, wherein the at least one arm on the first side of the spine and the at least one arm on the second side of the spine each comprise an attachment point for attaching the arms to a bone.

3. The plate of claim 2, wherein the attachment point comprises a screw hole defined by an inner surface configured to engage the head of one of a plurality of bone screws.

4. The plate of claim 2, wherein the attachment point comprises a threaded screw hole defined by a threaded inner surface configured to lockably engage one of a plurality of locking bone screws.

5. The plate of claim 2, wherein the at least one arm on the first side of the spine and the at least one arm on the second side of the spine each comprise a rigid rounded tab extending laterally from the spine perpendicular to the central axis of the spine.

6. The plate of claim 1, wherein:
the thickened ridge comprises generally smooth, elevated ridge of material symmetrically distributed about the central axis of the spine spanning from the first end of the spine to the second end of the spine, the thickened ridge being thickest in the center of the spine and tapering off in thickness as the thickened ridge extends laterally toward the plurality of arms; and
the at least one groove comprises a pair of recessed channels symmetrically distributed about the central axis of the spine spanning from the first end of the spine to the second end of the spine.

7. The plate of claim 1, wherein the plate comprises a cross-sectional curvature in a plane perpendicular to the central axis.

8. The plate of claim 7, wherein compression of the at least one groove draws the at least one arm on the first side of the spine toward the at least one screw hole on the second side of the spine and increases the cross-sectional curvature of the spine.

9. The plate of claim 1, wherein compression of the at least one groove increases the axial stiffness of the plate along the central axis of the plate.

10. A plate for securing bones together, comprising:
an elongate spine comprising:
a thickened ridge, spanning along a length of the spine parallel to the central axis of the spine;
a first surface of the spine comprising at least one groove spanning along a length of the spine parallel to the central axis of the spine; and
a second surface, opposite the first surface, comprising the thickened ridge; and
a plurality of arms extending laterally from the spine, the plurality of arms comprising at least one arm on a first side of the spine and at least one arm on a second side of the spine;
wherein at least one of the at least one arm on the first side of the spine and at least one of the at least one arm on the second side of the spine each comprises an attachment point for attaching the arms to a bone, the attachment point comprising a hole defined by an inner surface configured to receive an attachment device.

11. The plate of claim 10, wherein the hole comprises a threaded screw hole defined by a threaded inner surface configured to lockably engage one of a plurality of locking bone screws.

12. The plate of claim 10, wherein:
the thickened ridge comprises generally smooth, elevated ridge of material symmetrically distributed about the central axis of the spine spanning from the first end of the spine to the second end of the spine, the thickened ridge being thickest in the center of the spine and tapering off in thickness as the thickened ridge extends laterally toward the plurality of arms; and
the at least one groove comprises a pair of recessed channels symmetrically distributed about the central axis of the spine spanning from the first end of the spine to the second end of the spine.

13. The plate of claim 10, wherein the plate comprises a memory shape material operable to compress the at least one groove when the plate is heated above a transformation temperature of the memory shape material.

14. The plate of claim 10, further comprising one or more screw holes disposed along the spine.

15. The plate of claim 10, wherein the spine is curved along the central axis to approximate the geometry of a joint structure.

16. A method for securing bones together, comprising:
attaching to a first bone and a second bone, a plate comprising:
an elongate spine comprising at least one groove spanning along a length of the spine parallel to a central axis of the spine, wherein:
a first surface of the spine comprises a thickened ridge spanning along a length of the spine parallel to the central axis of the spine; and
a second surface, opposite the first surface, comprises the at least one groove; and
a plurality of arms extending laterally from the spine, the plurality of arms comprising at least one arm on a first side of the spine and at least one arm on a second side of the spine.

17. The method of claim 16, wherein:
the at least one arm on the first side of the spine and the at least one arm on the second side of the spine each comprise an attachment point, the attachment point comprising a screw hole defined by an inner surface configured to engage a head of a bone screw; and
the step of attaching comprises screwing the bone screw into the screw hole on the at least one arm on the first side of the spine or the at least one arm on the second side of the spine until the bone screw engages the threaded screw hole.

18. The method of claim 17, further comprising compressing the at least one groove to draw the at least one screw hole on the first side of the spine toward the at least one screw hole on the second side of the spine.

19. The method of claim 18, wherein the compressing step occurs after the attaching step.

20. The method of claim 18, wherein the compressing step occurs before the attaching step.

21. The method of claim 18, wherein the plate comprises a memory shape material operable to compress the at least one groove when the plate is heated above a transformation temperature of the memory shape material, and further comprising:

mechanically deforming the plate such that the memory shape material is operable to compress the at least one groove once the plate is heated above the transformation temperature.

* * * * *